US008776298B2

(12) United States Patent
Fritsch et al.

(10) Patent No.: US 8,776,298 B2
(45) Date of Patent: Jul. 15, 2014

(54) CLEANING SECTION OF AN ELECTRIC ORAL HYGIENE DEVICE

(75) Inventors: Thomas Fritsch, Eppstein (DE); Ulrich Stoerkel, Bad Nauheim (DE)

(73) Assignee: Braun GmbH, Kronberg (DE)

( * ) Notice: Subject to any disclaimer, the term of this patent is extended or adjusted under 35 U.S.C. 154(b) by 215 days.

(21) Appl. No.: 13/328,183

(22) Filed: Dec. 16, 2011

(65) Prior Publication Data
US 2012/0159722 A1 Jun. 28, 2012

(30) Foreign Application Priority Data

Dec. 22, 2010 (EP) .................................... 10015966

(51) Int. Cl.
*A61C 17/22* (2006.01)
*A61C 17/34* (2006.01)

(52) U.S. Cl.
USPC ........................................................ 15/22.1

(58) Field of Classification Search
USPC ................................. 15/22.1, 22.4
See application file for complete search history.

(56) References Cited

U.S. PATENT DOCUMENTS

| 5,504,959 A | | 4/1996 | Yukawa et al. | |
|---|---|---|---|---|
| 5,778,474 A | * | 7/1998 | Shek | 15/22.1 |
| 5,850,655 A | * | 12/1998 | Gocking et al. | 15/28 |

FOREIGN PATENT DOCUMENTS

| DE | 10229148 | * | 1/2004 |
|---|---|---|---|
| DE | 20 2009 000168 U1 | | 4/2009 |
| EP | 460610 | * | 12/1991 |
| FR | 2840784 | * | 12/2003 |
| WO | 99/12492 | * | 3/1999 |

OTHER PUBLICATIONS

European Search Report for EP 10 01 5966—dated Jun. 29, 2011.
PCT Search Report for PCT/IB2011/055822—dated Apr. 18, 2012.

* cited by examiner

*Primary Examiner* — Mark Spisich
(74) *Attorney, Agent, or Firm* — John P. Colbert

(57) ABSTRACT

A cleaning section of an oral hygiene device is disclosed. The cleaning section includes a cleaning element carrier mounted for oscillatory rotation around a carrier rotation axis; a gear unit arranged for being coupled to a drive shaft of a handle of the oral hygiene device, which drive shaft defines a drive shaft rotation axis in an attached state, and the gear unit further having an actuation element for transferring motion from the drive shaft to the cleaning element carrier during operation. The carrier rotation axis is parallel to the drive shaft rotation axis and is disposed at a distance to the drive shaft rotation axis.

10 Claims, 6 Drawing Sheets ly inclined to the drawings are illustrative
CLEANING SECTION OF AN ELECTRIC ORAL HYGIENE DEVICE

CROSS REFERENCE TO RELATED APPLICATIONS

This application claims the benefit of European Patent Convention Application No. 10015966.4, filed Dec. 22, 2010, the substance of which is incorporated by reference in its entirety herein.

FIELD OF THE INVENTION

The present disclosure is directed to a cleaning section of an electric oral hygiene device. More particularly, the present disclosure is directed to a cleaning section including a cleaning element carrier mounted for oscillatory rotation.

BACKGROUND OF THE INVENTION

Cleaning sections of oral hygiene devices such as electric toothbrushes are known, where a moving cleaning element carrier is arranged to be coupled to a drive shaft of a handle of the electric toothbrush. It is known that the drive shaft provides the oscillatory rotation movement, where the drive shaft oscillates with a certain fixed maximum oscillation angle around a center position.

SUMMARY OF THE INVENTION

In one embodiment, a cleaning section of an oral hygiene device is provided. The cleaning section includes a cleaning element carrier mounted for oscillatory rotation around a carrier rotation axis; a gear unit arranged for being coupled to a drive shaft of a handle of the oral hygiene device, which drive shaft defines a drive shaft rotation axis in an attached state, and the gear unit further having an actuation element for transferring motion from the drive shaft to the cleaning element carrier during operation. The carrier rotation axis is parallel to the drive shaft rotation axis and is disposed at a distance to the drive shaft rotation axis.

In another embodiment, an electric oral hygiene device is provided. The electric oral hygiene device includes a handle; and a cleaning element carrier mounted to the handle for oscillatory rotation around a carrier rotation axis, the cleaning element carrier including a gear unit arranged for being coupled to a drive shaft of a handle of the oral hygiene device, which drive shaft defines a drive shaft rotation axis in an attached state, and the gear unit further having an actuation element for transferring motion from the drive shaft to the cleaning element carrier during operation; wherein the carrier rotation axis is parallel to the drive shaft rotation axis and is disposed at a distance to the drive shaft rotation axis.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

Figure 1:
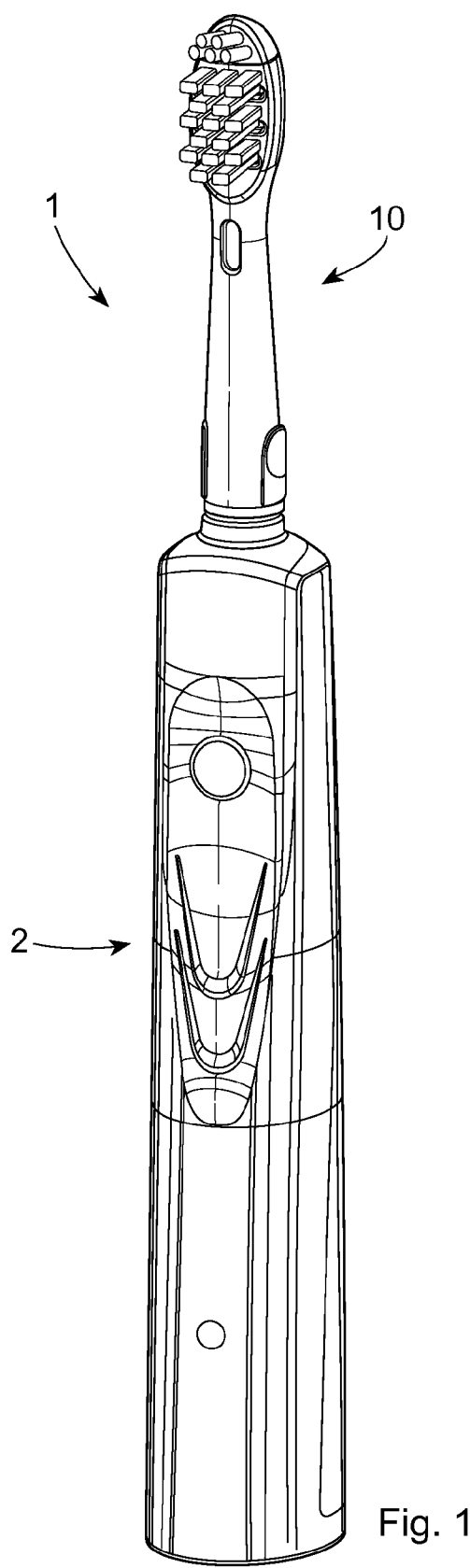
FIG. 1 is an example depiction of an electric oral hygiene device toothbrush including an example cleaning section according to embodiments shown and described herein.
Figure 7:
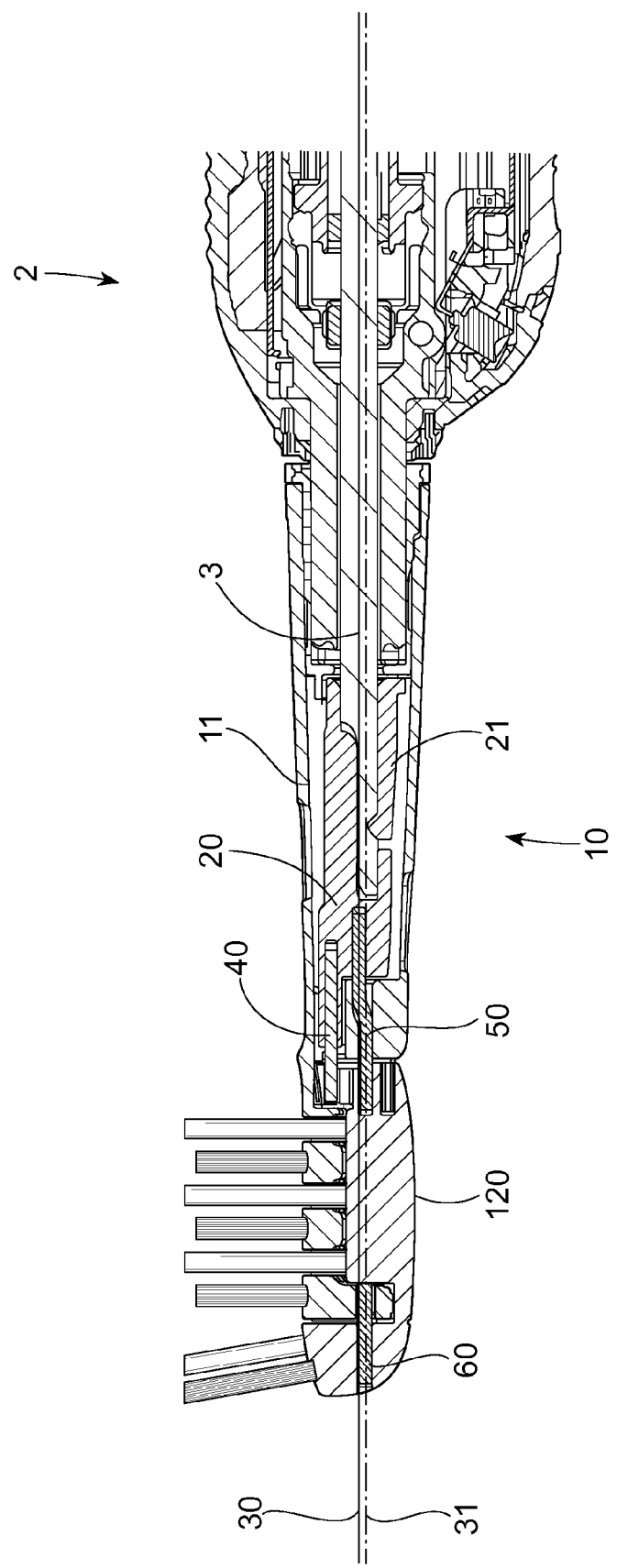
FIG. 7 is a longitudinal cut through an example oral hygiene device including a cleaning section as shown in FIG. 3 and a handle (only partly shown).

FIG. 1 is a depiction of an example electric oral hygiene device 1 (here realized as an electric toothbrush) including a cleaning section 10 (here realized as a brush section) and a handle 2. In one embodiment, the cleaning section 10 may be a detachable part. A longitudinal cut through an oral hygiene device is shown in FIG. 7.

Figure 2:
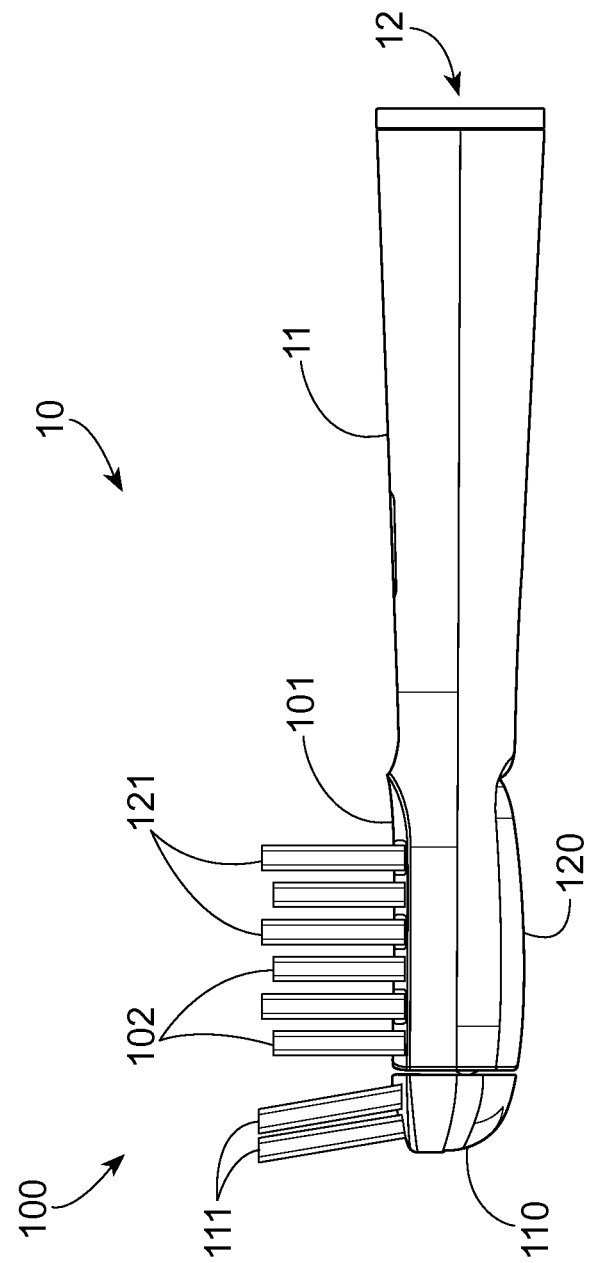
FIG. 2 is a side view onto an example cleaning section toothbrush according to embodiments shown and described herein.

FIG. 2 is a side view onto a cleaning section 10 similar to the one as shown in FIG. 1 but being in a detached state. The cleaning section 10 (here realized as a detachable brush section) including a housing 11 having a tubular neck section that is essentially cylindrical but slightly tapers towards a brush head 100. The cleaning section 10 has an opening 12 arranged to receive a coupling section of a handle of an electric toothbrush (FIG. 7 shows a longitudinal cut through a top part of a handle 2 and an attached cleaning section 10). The brush head 100 comprises in the shown example a static carrier 101 that is an integral part of the housing 11 and a cleaning element carrier 120 that is movably mounted underneath the static carrier 101, which cleaning element carrier 120 is here integral with (or at least fixedly connected to) a front carrier 110. Here, several rows of cleaning elements 102 realized as bristle tufts are mounted on the static carrier 101 and several rows of cleaning elements 121 also realized as bristle tufts are mounted on the movably mounted cleaning element carrier 120, where the rows of static cleaning elements 102 and rows of movable cleaning elements 121 are alternately arranged and the rows of movable cleaning elements 121 extend through apertures in the static carrier 101. Further front cleaning elements 111 realized as bristle tufts are mounted on the front carrier 110. It is noted that the kind of cleaning elements shown is just an example and that further in an alternative embodiment no cleaning elements are mounted on the static carrier 101 (i.e. the static carrier itself is an optional feature). Additionally, the front carrier 110 is an optional feature.

FIG. 2 shows an example embodiment of a proposed cleaning section. Other embodiments may not have static cleaning elements and the movable carrier may be positioned in a respective aperture of the housing. Further embodiments may have elastomeric cleaning elements instead of or in addition to bristle tufts. There may be only a single cleaning element, for example, an interdental cleaning element, mounted on the movable cleaning element carrier etc. Generally, a cleaning section as proposed comprises a movably mounted cleaning element carrier to which cleaning elements are mounted.

Figure 3:
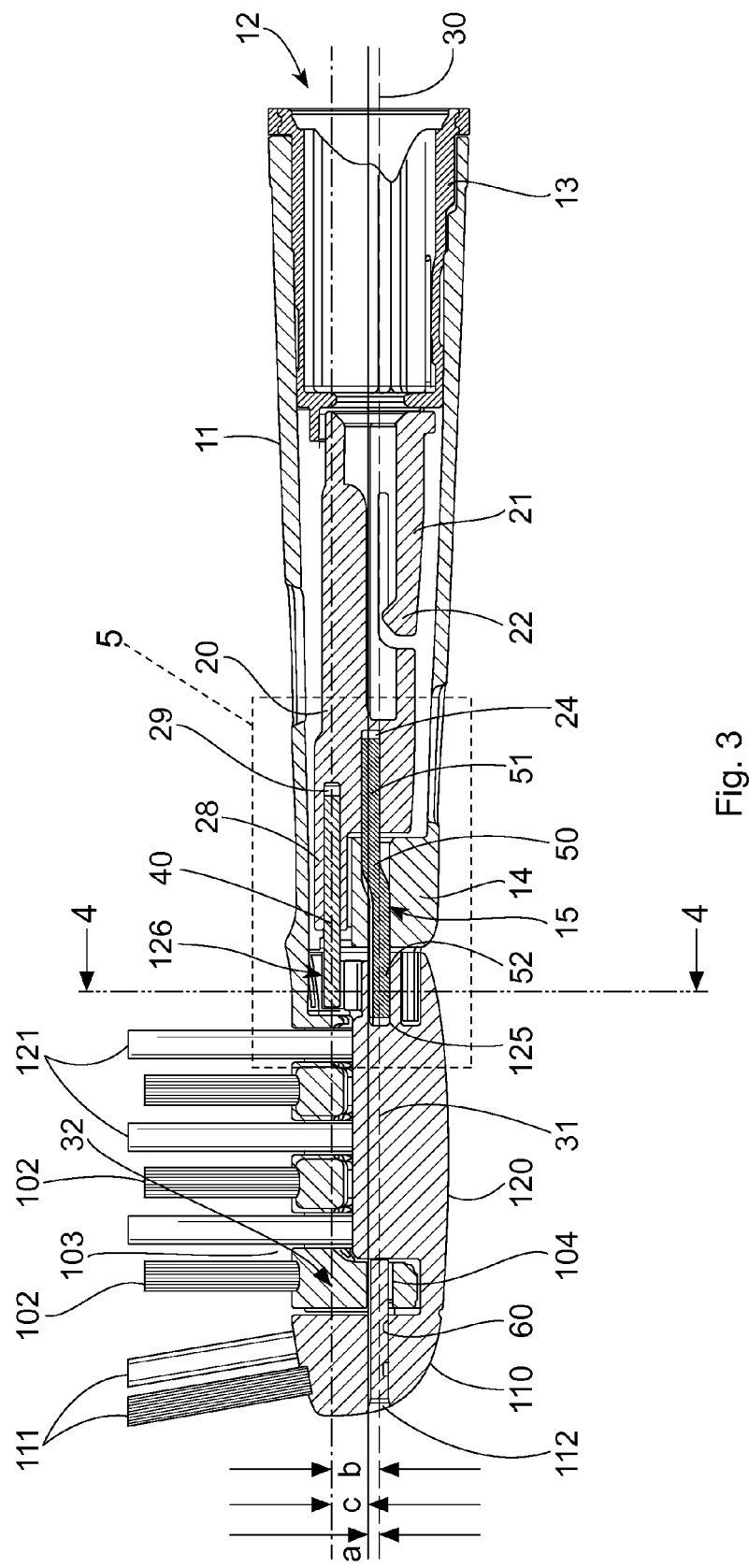
FIG. 3 is a longitudinal cut through the centre of the cleaning section shown in FIG. 2.

FIG. 3 is a center longitudinal cut through the example cleaning section 10 as shown in FIG. 2. The housing 11 has a hollow neck section in which a shaft element 20 and a non-detachably attached insert element 13 are disposed. A driving shaft and a neck part of a handle of an oral hygiene device can be inserted into the hollow neck section through opening 12. As will be clear in connection with FIG. 7, in the present embodiment a snap nose 22 of a snap hook 21 of the shaft element 20 will snap into a respective V-shaped groove of the drive shaft of the handle and further the neck part of the handle will positively fit into the insert element 13. The shaft element 20 is movably mounted at the housing 11 by a shaft pivot element 51, which shaft pivot element 51 extends on a first side into a bore 24 in the shaft element 20 and on a second side into a bore 15 of a support structure 14 that is an integral part of the housing 11. The shaft pivot element 51 extends along an axis that coincides with the drive shaft rotation axis 30 that is defined by the drive shaft of the handle of an oral hygiene device in the attached state of the cleaning section 10 (as can be principally understood from FIG. 7).

Hence, the shaft pivot element 51 is arranged centrically with the drive shaft rotation axis 30. An actuation element 40, here realized as a metal pin, is mounted on one side in a bore 29 of a protrusion 28 of the shaft element 20 and is supported at the other side at a mounting structure 126 of the cleaning element carrier 120. The actuation element 40 extends along an actuation axis 32 that is parallel to the drive shaft rotation axis 30 and that is disposed at a distance c to the drive shaft rotation axis 30 (i.e. the actuation element 40 is arranged eccentrically with respect to the drive shaft rotation axis 30. Hence, when the shaft element 20 is rotated in an oscillating manner around the drive shaft rotation axis 30 during operation, the actuation element 40 moves along a circular segment around the drive shaft rotation axis 30 and thus transfers movement from the shaft element 20 to the movably mounted cleaning element carrier 120. The movably mounted cleaning element carrier 120 is mounted on a first side at the housing 11 with a carrier pivot element 52 and at a second side with a mounting pivot element 60. The carrier pivot element extends on a first side into a bore 15 in a support structure 14 (which here is an integral part of the housing 11) and on a second side into a bore 125 of the cleaning element carrier 120.

The mounting pivot element extends on a first side into a bore 112 provided in the front carrier 110 and on a second side into a bore 104 provided in the static carrier 101. In the shown example cleaning section 10, the mounting pivot element 60 is realized as a mounting pin, for example, a metal mounting pin, and the carrier pivot element 52 is realized integrally with the shaft pivot element 51 as a cranked pivot element 50, where the cranked pivot element 50 is here realized as a cranked metal pin. The cranked pivot element 50 is supported at the housing 11 in a bore 15 of the support structure 14. The carrier pivot element 52 and the mounting pivot element 60 extend along a carrier axis 31 and thus define the rotation axis of the cleaning element carrier 120. The carrier axis 31 is parallel to the drive shaft rotation axis 30 and is disposed at a distance a to the drive shaft rotation axis 30 such that the distance b between the carrier axis 31 and the actuation axis is in the shown embodiment larger than the distance c.

In some embodiments, the distance a may be in the range of between about 0.1 mm and about 3 mm, and in another embodiment between about 0.2 mm and about 0.9 mm. A single cranked pivot element 50 being an integral part realizing the shaft pivot element and the carrier pivot element allows realizing such relatively small distances between the drive shaft rotation axis 30 and the carrier axis 31 by the crank in the cranked pivot element 50, which introduces a step that may be smaller than the diameter of the pin that is used to manufacture the cranked pivot element 50 in the shown example. FIG. 3 shows the centered rest position of the movably mounted cleaning element carrier 120 in which all three axes 30, 31, and 32 lie in a single plane. During operation, when the shaft element 20 is driven into an oscillating rotation around drive shaft rotation axis 30, the shaft element 20 will rotate around shaft pivot element 51 and the actuation element 40 is moved along a circular segment around the drive shaft rotation axis 30. The actuation element 40 is essentially play-free mounted at the movably mounted cleaning element carrier 120 and thus will force the cleaning element carrier 120 into an oscillating rotation around the carrier axis 31 that is defined by the carrier pivot element 52 and the mounting pivot element 60.

As the distance b between the carrier axis 31 and the actuation axis 32 is larger than the distance c between drive shaft rotation axis 30 and actuation axis 32, the oscillation angle provided by the drive shaft (i.e. the drive shaft oscillates around a center rest position with an angle of $\pm\beta$ degrees, where $\beta$ might be in the range of about 2 degrees to about 60 degrees, in another embodiment between about 10 degrees and about 30 degrees) is reduced by the example gear arrangement (i.e. the cleaning element carrier 120 will oscillate around the carrier axis 31 with a maximum angle of $\pm\gamma$ degrees, where $\gamma<\beta$. The relation between the distances c and b and the respective maximum oscillation angles is given by: $b \cdot \sin(\gamma/2) = c \cdot \sin(\beta/2)$. Thus, it is clear that by a different gear arrangement, where the carrier axis 31 is closer to the actuation axis 32 than the drive shaft axis 30 (i.e. the distance b<distance c) the maximum oscillation angle as provided by the oscillating drive shaft is increased. As the maximum oscillation angle of the drive shaft may be fixed, a gear arrangement as proposed allows adapting the oscillation angle of the cleaning element carrier. In the shown example, a smaller oscillation angle allows building a head having a relatively low height, which may be preferred by some users, while it leads on the other hand to a lower average velocity of the free ends of the bristles as would be the case in a case with distance a=0. A larger oscillation angle allows having a higher velocity of the free ends of the bristles in case the oscillation frequency is fixed, which may lead to better cleaning results, but may on the other hand irritate the gums by the higher brushing speed.

As can be seen in the embodiment shown in FIG. 3, cleaning elements 102 realized as bristle tufts are mounted on the static carrier 101 and cleaning elements 121 realized as bristle tufts are mounted on the movably mounted cleaning element carrier 120. Further, cleaning elements 111 realized as bristle tufts are mounted on the front carrier 110, which front carrier 110 is integral with the movably mounted cleaning element carrier 120. The cleaning elements 121 mounted on the cleaning element carrier 120 extend though apertures 103 provided in the static carrier 101. In general, an embodiment is described where a movably mounted cleaning element carrier is coupled to a gear unit such that in an attached state during operation a drive shaft of a handle of an electric oral hygiene device provides a certain maximum oscillation angle that is adapted by the gear unit to a smaller or larger oscillation angle around a carrier axis that is parallel to the drive shaft axis and that is disposed at a distance to the drive shaft axis.

Figure 4:
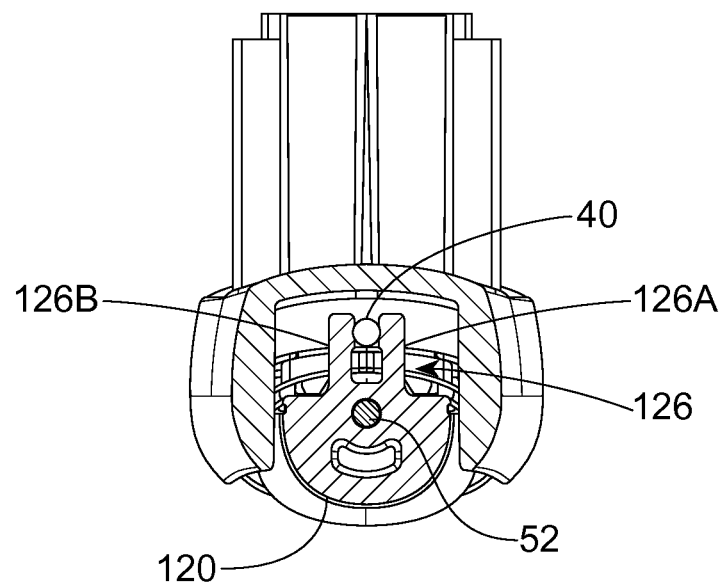
FIG. 4 is a cross sectional cut through the cleaning section shown in FIG. 2 along line B-B.

FIG. 4 shows a cross sectional cut through the cleaning section as shown in FIGS. 2 and 3, where the cut was taken along line B-B as indicated in FIG. 3. Carrier pivot element 52 defines the carrier axis around which the cleaning element carrier 120 will be driven. The actuation element 40 is mounted in a mounting section 126, which in the shown example is realized as a U-shaped fork that clamps the actuation element 40 close to the free ends of the fork arms 126A and 126B. The fork arms 126A and 126B may in particular be shaped to tightly accommodate the actuation element 40, for example, the fork arms 126A and 126B may be concavely shaped on their inner side such that the here cylindrical actuation element 40 positively fits into the concave cut-outs. In the shown example, the original distance between the fork arms 126A and 126B at the location where the actuation element 40 is to be mounted is slightly smaller in diameter than the diameter of the actuation element 40. Thus, when the actuation element 40 is mounted between the fork arms 126A and 126B, the fork arms are biased against the actuation element (i.e. the fork arms 126A and 126B exert a spring force on the actuation element 40). During operation, toothpaste may penetrate in between the fork arms and the actuation element and due to the movement of the actuation element the abrasive particles contained in toothpaste may abrade one or both of the mounting partners. In particular, the cleaning element carrier 120 and the mounting section 126 that is here an integral part of the cleaning element carrier may be made from a plastic material (for example, POM or ASA) and may thus be faster abraded than the actuation element, which may be made from metal (for example, stainless steel). A mounting of the actuation element under a spring load may thus compensate abrasion of the mounting section insofar as slight abrasion may not immediately lead to clearances between the mounting partners and thus increased noise generation during operation due to such clearances may be reduced. It may thus be considered an individual aspect of the present disclosure that a cleaning section is provided with a pivot element (here: the actuation element) that is mounted at least on a first side under a spring load.

Figure 5:
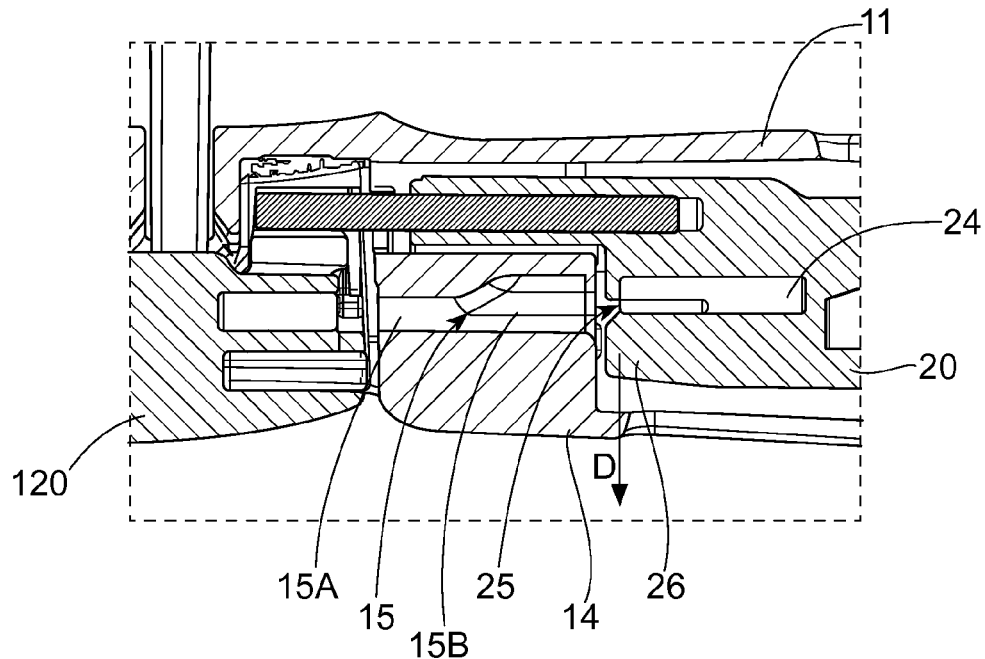
FIG. 5 shows a detail AB identical in position to detail A shown in FIG. 3, but where the cranked pivot element is removed in order to show details of the mounting bore.

FIG. 5 is a depiction of a detail AB which is identical in position to detail A indicated in FIG. 3 but without the cranked pivot element 50. The bore 15 in the support structure 14 that here is an integral part of the housing 11 has a larger sized bore section 15A facing the shaft element 20 and a smaller sized bore section 15B facing the cleaning element carrier 120. The cranked pivot element may be mounted from the side facing the shaft element 20, so that after the mounting process, the cranked pivot element is supported in the bore 15 as is shown in FIG. 3. The shaft element 20 has a bore 24 for accommodating a part of the shaft pivot element portion of the cranked pivot element in the mounted state. Here, the bore 24 in the shaft element 20 has two laterally positioned slits (only one slit 25 can be seen in this longitudinal cut section) that extend from about a longitudinal center position in the bore to the front of the bore 24. The slits 25 make the tongue-like front part 26 of the shaft element 20 flexible so that the front part 26 can be moved into a direction D as indicated in FIG. 5.

The bore 24 is here slightly tapered at the front to allow easy insertion of the shaft pivot element into the bore 24. The bore 24 may be designed with a slightly smaller diameter at the front part 26 such that insertion of the shaft pivot element bends the front part 26 into direction D. In another embodiment, the tongue-like front part 26 has a thickened portion at the front tip that projects radially into the bore 24 that reduces the diameter of the bore 24. The tongue-like front part 26 then exerts a spring force onto the shaft pivot element in the mounted state. As was explained with respect to FIG. 4, such mounting under spring load can compensate for abrasion of one or more of the mounting partners under the influence of toothpaste such that the generation of clearances between the mounting partners may be delayed.

In general, mounting partners mounted under a spring load may be designed such that the generation of clearances and thus the generation of unwanted noise during operation may be delayed for a certain operation time. The more material is abraded the lower the spring force becomes until no spring force is exerted anymore and clearances are generated. The design parameters can be based, for example, on measuring abrasion of the material of the mounting partners over time under the influence of a typical toothpaste. As a typical usage time per day per cleaning section (i.e. per user) is about 2 minutes-12 minutes and as typical cleaning sections typically hold about 1.5-6 month until they are worn out, the spring load (i.e. the deformation of a flexible mounting partner) can be designed to compensate abrasion in a range of between about 90 minutes of operation time to about 2160 minutes of operation time. A typical average brushing time per day may be 4 minutes and a typical wear-out time of the cleaning section may be 3 month, so that a compensation of about 360 minutes may be chosen in some embodiments, but any other time from the above range may be chosen as well. Mounting under a spring load may be implemented for one, several or all of the pivoting elements (including the actuation element) and may be implemented individually on one or on two sides. In particular, the here described mounting of at least a pivoting element (for example, the actuation element) under a spring force may be considered to have a separate value in itself as was explained above.

Hence, in view of one aspect of the present disclosure, a cleaning section has a gear unit that includes a pivot element (for example, an actuation element as was described with reference to FIG. 4 or a pivot element as was described with reference to FIG. 5), which pivot element is at least on a first side mounted under a spring load. Such mounting under a spring load has the effect that material abrasion of the mount or the pivot element that will eventually occur over time—in particular when, for example, toothpaste reaches the mounting location during operation—may be compensated for. Instead, when a form-fit mounting is used, this may relatively swiftly lead to clearances and thus noise and reduced functionality are more likely to occur earlier, i.e. prior to a typical wear-out time of a cleaning section and may thus irritate a user. If the pivot element is—as proposed—mounted under a spring load, the abrasion may lead to a reduced spring force over time, but there is less likelihood that clearances and thus noise and/or reduction of functionality occur swiftly.

Figure 6:
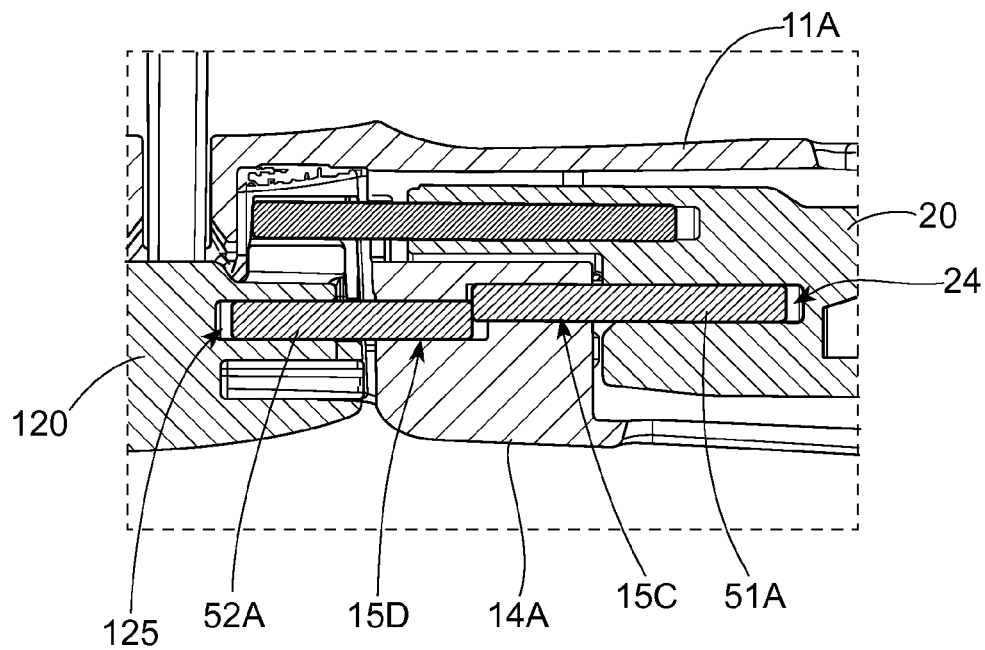
FIG. 6 shows a detail AC identical in position to detail A shown in FIG. 3 of a different example embodiment of a proposed cleaning section where instead of a cranked pivot element a shaft pivot element and a carrier pivot element are utilized.

FIG. 6 is a depiction of detail AC that is identical in position with detail A indicated in FIG. 3 but shows a different example realization. Here, the shaft pivot element 51A and the carrier pivot element 52A are separate pivot elements. The shaft pivot element 51A is mounted on a first side in bore 24 in shaft element 20 and on a second side in bore 15C in a support structure 14A that is an integral part of the housing 11A. The carrier pivot element 52A is mounted on a first side in a bore 15D provided in the support structure 14A and on a second side in a bore 125 in the cleaning element carrier 120. Even though the bores 15C and 15D are shown as connected bores forming a continuous bore in the support structure 14A, the bores 15C and 15D can alternatively also be realized as not connected bores. The example shown in FIG. 6 can be realized by two simple metal pins forming the shaft pivot element 51A and carrier pivot element 52A but the individual support length of the separate pivot elements in the support structure 14A is in the shown example shorter than the overall support length of the cranked pivot element 50 shown in FIG. 3, as in the shown example the distance between the drive shaft rotation axis and the carrier rotation axis is less than the diameter of the pins realizing the two pivot elements 51A and 52A.

FIG. 7 is a longitudinal cut through the cleaning section 10 as shown in FIG. 3 when being attached to a handle 2 (only partly shown) of an example electric oral hygiene device (here realized as an electric toothbrush). The handle 2 comprises a drive shaft 3 that is coupled to a drive system (for example, including an energy source, a motor and a gear arrangement) that drives the drive shaft in an oscillating rotary manner around its longitudinal center axis that defines the drive shaft rotation axis 30. The drive shaft 3 has, as is known in the art, in the shown example a flat front portion and a V-shaped groove provided on a side opposite to the flattened portion so that the flattened portion essentially positively fits within a respective opening in the shaft element 20 and the snap nose of the snap hook 21 snaps into the V-shaped groove when the cleaning section 10 is being attached to the handle 2. During operation, when the drive shaft is driven into an oscillatory rotation around the drive shaft rotation axis 30, the shaft element 20, which is essentially play-free coupled to the drive shaft 3 with respect to rotational movements around drive shaft rotation axis 30, is thus also driven into the same oscillatory rotation around drive shaft rotation axis 30. The actuation element 40 then moves on a circular segment around the drive shaft rotation axis 30. As the actuation element 40 is mounted essentially play-free to the cleaning element carrier 120 (in the above with respect to FIG. 4 discussed example the actuation element 40 is mounted to the carrier element 120 under a spring force), the cleaning element carrier 120 is driven into a similar oscillatory rotation. As the cleaning element carrier 120 is mounted to the housing 11 by a carrier portion of the cranked pivot element 50 and by the mounting pivot element 60, which both extend along the carrier rotation axis 31, the oscillatory rotation of the cleaning element carrier 120 happens around the carrier rotation axis 31 and thus the cleaning element carrier 120 moves with a smaller maximum oscillation angle with respect to the carrier rotation axis 31 in the shown example as the drive shaft 3 does with respect to the drive shaft rotation axis 30.

In accordance with a further aspect of the present disclosure, noise reduction during operation is reduced by an alternative or additional measure that will be explained in the following. In a brush design as shown in the above described figures, the oscillating/rotating cleaning element carrier tends—in particular in a non-loaded state, i.e. when the cleaning elements are not pressed against the teeth or oral tissue—to slightly overshoot in its oscillating movement. When the movable cleaning element carrier overshoots, it may happen that the cleaning element carrier contacts at least a part of the housing, which may lead to increased noise and also to wear of the colliding parts. In order to make such collisions less likely, provision is made that at least one aperture in the housing through which at least a cleaning element extends has a width in the oscillation direction that is slightly smaller than the width that would be required to allow for free oscillation of the cleaning element even in case of angular overshoots. In such a case, the overshoot movement is not (or at least not only) stopped by a collision between the cleaning element carrier and the housing, which both may be made from a hard plastic material, but by a collision of a cleaning element with the sidewall of the aperture. As the cleaning element may in particular be made from a soft plastic material (for example, a rubber-like elastomer) or as the cleaning element may be realized as a bristle tuft comprising a large number of bristles (for example, 10-100 bristles) so that the cross section of the tuft can deform during such a collision even if the material of the bristles itself is relatively rigid (for example, the bristles can be made of a polyamide), the collision between the cleaning element and sidewall of the aperture is relatively soft and elastically slows down the overshoot movement with a relatively low noise generation. According to another aspect, the sidewall of the aperture may at least partly be made of an elastomeric material. According to the above discussed aspect of the disclosure there is hence provided an oral cleaning section having a housing that has at least an aperture, a cleaning element carrier having a cleaning side to which at least a cleaning element is mounted, wherein the cleaning element carrier is mounted for oscillation around a carrier axis with a maximum oscillation angle and the cleaning element carrier is also mounted such that the cleaning element extends through the aperture, wherein further the aperture is sized such that an overshoot oscillation (i.e. an oscillation with an angle larger than the maximum oscillation angle) of the cleaning element carrier leads to a collision of the cleaning element with a sidewall of the aperture.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A cleaning section of an oral hygiene device, comprising:
   a cleaning element carrier mounted for oscillatory rotation around a carrier rotation axis, the cleaning element carrier being mounted to a housing of the cleaning section via a mounting pivot element and a carrier pivot element, both elements extending along the carrier rotation axis;
   a shaft element arranged for being coupled to a drive shaft of a handle of the oral hygiene device, which drive shaft defines a drive shaft rotation axis in an attached state, and which shaft element is mounted to the housing of the cleaning section via a shaft pivot element that extends along the drive shaft rotation axis; and an actuation element for transferring motion from the drive shaft to the cleaning element carrier during operation;

wherein the carrier rotation axis is parallel to the drive shaft rotation axis and is disposed at a distance to the drive shaft rotation axis; and wherein the carrier pivot element and the shaft pivot element are integrally realized by a cranked pivot element.

2. The cleaning section according to claim 1, wherein the distance between the carrier rotation axis and the drive shaft rotation axis is between about 0.1 mm and about 3 mm.

3. The cleaning section according to claim 1, wherein the actuation element extends along an actuation element axis that is parallel to the drive shaft rotation axis and that is disposed at a distance to the drive shaft axis.

4. The cleaning section according to 1, wherein the cranked pivot element is supported in a support structure of the housing of the cleaning section.

5. The cleaning section according to claim 1, wherein the actuation element is mounted at least to the cleaning element carrier under a spring load.

6. The cleaning section according to claim 5, wherein the spring load is chosen such that any abrasion affecting causing a potential play in the mounting of the actuation element can be compensated for a predetermined period, the predetermined period being in a range of between about 90 minutes of operation time and about 2160 minutes of operation time.

7. The cleaning section according to claim 1, wherein the cranked pivot element is mounted at least to the shaft element under a spring load.

8. The cleaning section according to claim 7, wherein in a centered rest position the actuation element acts on the cleaning element carrier at an actuation point and the minimum distance between the carrier rotation axis and the actuation point is larger than the minimum distance between the drive shaft rotation axis and the actuation point.

9. The cleaning section according to claim 1, including at least one of the pivot elements being mounted at least on a first side under a spring load.

10. The cleaning section according to claim 1, further comprising:

the housing has at least one aperture;

wherein the cleaning element carrier has a cleaning side to which at least a cleaning element is mounted, wherein the cleaning element carrier is mounted for oscillation around the carrier rotation axis with a maximum oscillation angle and the cleaning element carrier is further mounted such that the cleaning element extends through the aperture, and wherein the aperture is sized such that an overshoot oscillation of the cleaning element carrier leads to a collision of the cleaning element with at least a sidewall of the aperture.

\* \* \* \* \*